United States Patent [19]

Ito et al.

[11] Patent Number: 4,913,698

[45] Date of Patent: Apr. 3, 1990

[54] AQUA-STREAM AND ASPIRATOR FOR BRAIN SURGERY

[75] Inventors: Haruhide Ito, Kanazawa; Akihiro Kitamura, Ishikawa, both of Japan

[73] Assignee: Marui Ika Company, Limited, Tokyo, Japan

[21] Appl. No.: 241,423

[22] Filed: Sep. 7, 1988

[30] Foreign Application Priority Data

Oct. 26, 1987 [JP] Japan .......................... 62-163367[U]
Mar. 2, 1988 [JP] Japan .......................... 63-49220

[51] Int. Cl.$^{4}$ .......................... A61B 17/20

[52] U.S. Cl. .......................... 604/22; 604/35; 604/43; 604/141

[58] Field of Search .................. 222/95, 389; 128/305; 604/22, 27, 35, 34, 43–45, 140, 141, 147

[56] References Cited

U.S. PATENT DOCUMENTS 3,429,313 2/1969 Romanelli .......................... 604/43
4,090,514 5/1978 Hinck et al. .......................... 222/95
4,576,593 3/1986 Mommer .......................... 604/34
4,690,762 9/1987 Veltrup .......................... 604/43

*Primary Examiner*—J. L. Kruter
*Attorney, Agent, or Firm*—Armstrong, Nikaido, Marmelstein, Kubovcik & Murray

[57] ABSTRACT

An aqua-stream and aspirator for crushing and removing brain tumors in cerbral surgery comprises a pressure chamber, a soft bottle filled with a sterilized saline solution and mounted within the pressure chamber, an irrigation tube connected at one end to an outlet of the soft bottle, an ejection needle removably connected to the other end of the irrigation tube via a swtich for controlling passage of the solution through the irrigation tube, and a suction tube extending parallel to the ejection needle. The pressure chamber is adapted to be pressurized with a harmless gas so as to compress the soft bottle to eject the solution in the soft bottle from the ejection needle. The ejection needle has a nozzle which is bent in such a manner that the solution ejected from the nozzle is directed toward a confronting inside wall of the tip of the suction tube.

6 Claims, 5 Drawing Sheets

14
12
58
62b
62c
64
62
62a
12a
42
44
60
48
49
46
40
50
52
54
56
41
6

AQUA-STREAM AND ASPIRATOR FOR BRAIN SURGERY

BACKGROUND OF THE INVENTION

1. Field of the Invention

The present invention relates to an aqua-stream and aspirator (AS and A) which is useful in crushing and removing brain tumors during the brain surgery.

2. Description of the Prior Art

Conventionally, a variety of surgical instruments, such as an electric knife, a laser knife, and a CAVITRON ultrasonic surgical aspirator (CUSA), for removing brain tumors has been developed and put to practical use. A problem in using a laser knife is that injuries due to local heat are inevitable in and around the incision line, thus producing a nasty smell and smoke, which would screen the operator's visual field. Further, the use of a laser knife necessitates the operator and nurse to wear glasses to protect their eyes from laser light. An electric knife is available for only a limited use. Partly because its hand-piece is large in size and heavy in weight, and partly because the action of ultrasonic wave would be spread to even adjacent normal tissue, a CUSA is not suitable for a delicate operation.

In addition, an aqua-stream and aspirator (AS and A) utilizing a water stream is known for hepatic surgery. However, in this prior apparatus, partly because its entire structure is large-sized, and partly because pressurized water is ejected perpendicularly to the surface the affected part, there is a fear that even normal tissue could be crushed. Consequently the prior apparatus cannot be used for a delicate and precise operation which is required such as in cerebral surgery.

SUMMARY OF THE INVENTION

It is therefore an object of the present invention to provide an improved aqua-stream and aspirator which is suitable for delicate and precise operation required such as in brain surgery.

Another object of the invention is to provide an aqua-stream and aspirator which is useful for crushing and removing brain tumors effectively with maximum safety.

A further object of the invention is to provide an aqua-stream and aspirator which is free from the risk of injuring adjacent normal tissue due to heat and hence from a nasty smell and smoke.

A still further object of the invention is to provide an aqua-stream and aspirator which is free from the fear that various germs could penetrate the tissue.

According to the present invention, an aqua-stream and aspirator for crushing and removing brain tumors in cerebral surgery comprises a pressure chamber, a soft bottle filled with a sterilized saline solution and mounted within the pressure chamber, an irrigation tube connected at one end to an outlet of the soft bottle, an ejection needle removably connected to the other end of the irrigation tube via a switch for controlling passage of the solution through the irrigation tube, and a suction tube extending parallel to the ejection needle. The pressure chamber is adapted to be pressurized with a harmless gas so as to compress the soft bottle to eject the solution of the soft bottle from the ejection needle, and the ejection needle has a nozzle which is bent in such a manner that the solution ejected from the nozzle is directed toward a confronting inside wall of the tip of the suction tube.

Many other objects, features and additional advantages of the present invention will become manifest to those versed in the art upon making reference to the following detailed description and the accompanying sheets of drawings in which a couple of structural embodiments incorporating the principles of the present invention is shown by way of illustrative example.

DETAILED DESCRIPTION

Figure 2:
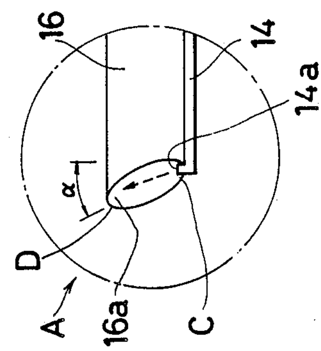
FIG. 2 is an enlarged view of a circled portion A in FIG. 1.
Figure 1:
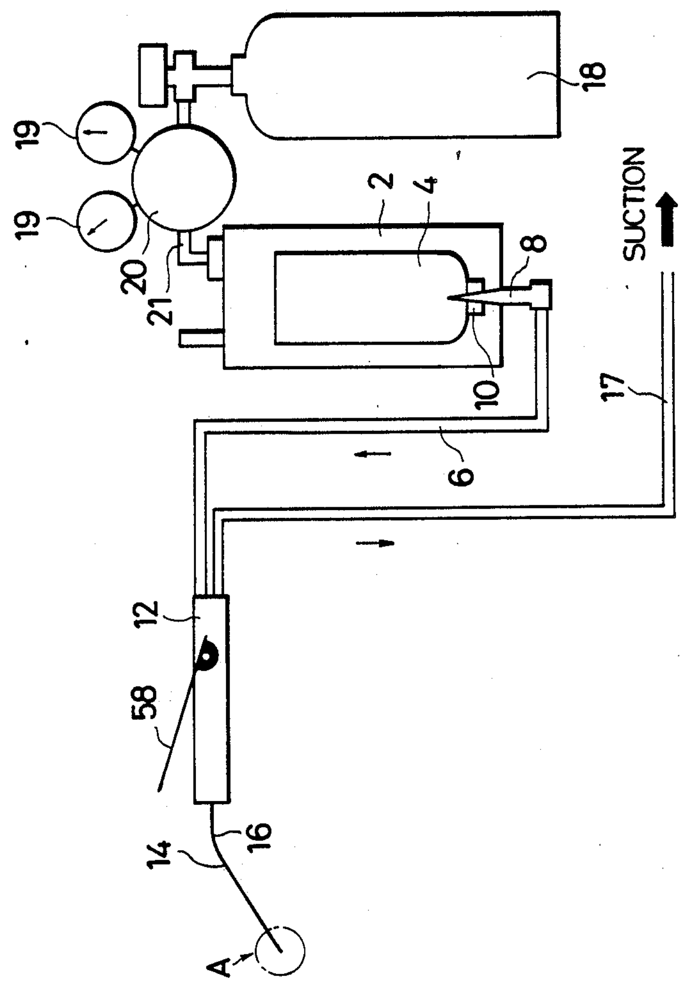
FIG. 1 is a schematic side elevational view of an aqua-stream and aspirator embodying the present invention.

The principles of the present invention are particularly useful when embodied in an aqua-stream and aspirator (hereinafter called "apparatus") such as shown in FIG. 1.

The apparatus generally comprises a pressure-proof cylinder constituting a pressure chamber 2, a soft bottle 4 of polyethylene filled with a sterilized saline solution and supported within the pressure chamber 2, an irrigation tube 6 connected at one end to an outlet 10 of the soft bottle 4, an on/off switch 12 connected to the other end of the irrigation tube 6 for controlling passage of the solution through the irrigation tube 6, and an ejection needle 14 attached to the forward end of the switch 12.

Figure 4:
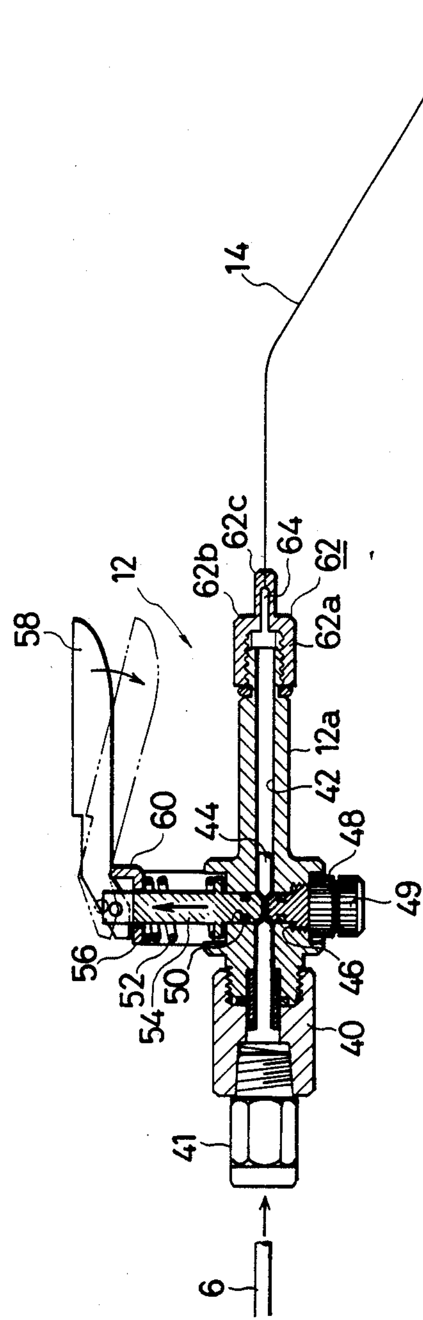
FIG. 4 is an enlarged cross-sectional view of an on/off switch of FIG. 1.
Figure 5:
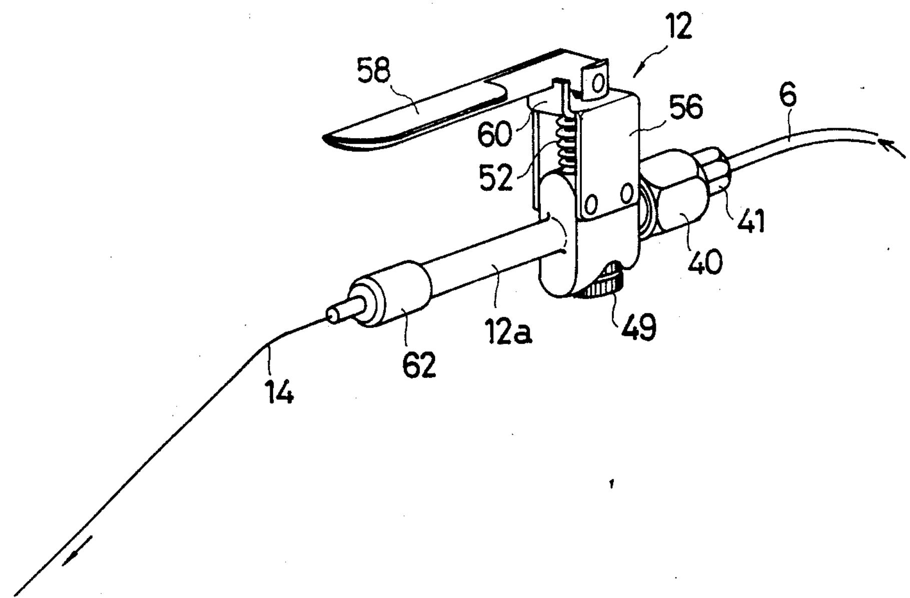
FIG. 5 is an enlarged perspective view of FIG. 4.

The ejection needle 14 is detachable from the switch 12 for replacement with a new one. Preferably, the ejection needle 14 is bent downwardly at an intermediate portion near the switch 12 at an angle of 115° to 155°, as shown in FIGS. 1, 4 and 5. A suction tube 16 extends parallel to the ejection needle 14.

Most important, the ejection needle 14 has at its tip a nozzle **14*a* which is bent at an angle $\alpha$ such that a jet of the solution ejected from the nozzle 14*a* strikes a confronting inside wall 16*a* of the tip of the suction tube 16. Although the tip of the suction tube 16 may have any desired shape, it preferably should be that an upper portion D of the suction-tube tip projects beyond a lower portion C near the nozzle 14*a* so as to receive the jet solution ejected from the nozzle 14*a***.

The suction tube 16 is connected to a suction pump (not shown) via a connection hose 17. The suction system may be a hanging type (to be hung on a wall of the operating room) or a portable type.

Designated by 18 is a gas cylinder charged with a gas harmless to a human body, such as oxygen gas or nitrogen gas. The gas cylinder 18 is connected to the pressure chamber 2 through a connection tube 21 having a pressure regulator 20 with two pressure gauges 19, 19. Thus the pressure chamber 2 is pressurized with the harmless gas so as to compress the soft bottle 4 so that the solution is forced out of the soft bottle 4 to pass through the irrigation tube 6 and the switch 12 and finally to be ejected from the nozzle 14a. The supply system of the harmless gas is not limited to the gas cylinder 18 as in the illustrated example; alternatively the pressure cylinder 2 may be connected to a pipe (not shown) lying in the wall of the operating room and leading to a gas source (not shown).

The switch 12 is operable by hand to open and close the passage of the solution to control the stream of solution to be ejected from the nozzle 14a. Alternatively the switch 12 may be operated by foot.

The gas to be supplied from the gas cylinder 18 into the pressure chamber 2 should be kept in very sanitary condition free of various germs. Preferably the pressure chamber 2 should be pressurized at a pressure of approximately 0 to 30 kg/cm$^2$, and practically the pressure chamber 2 is pressurized at a pressure of approximately 5 to 20 kg/cm$^2$.

The nozzle 14a of the ejection needle 14 has a mouth of approximately 0.1 to 0.12 mm in inside diameter so that the solution can be ejected from the nozzle 14a in a very small stream. Further, the nozzle 14a is bent at an angle $\alpha$, e.g. 15°, such that the solution ejected from the nozzle 14a strikes the confronting inside wall 16a of the suction tube 16. For under the affected part such as a brain tumor there exists the brain tissue which should not be crushed, if the nozzle 14a were in a straight form rather than in a bent form, or if the nozzle 14a were inadequately bent, the solution ejected from the nozzle 14a could not strike the confronting inside wall 16a of the suction tube 16, thus resulting in the crush of even normal tissue due to the direct jetting of the solution. The amount of sucking force of the suction tube 16 may be 0 to 500 mmHg, preferably 100 to 500 mmHg.

In use, as the suction nozzle 16 and the nozzle 14a of the ejection needle 14 is put on an affected or focal tissue N such as a brain tumor, the brain tumor N is partially sucked into the tip of the suction tube 16 and, at the same time, a jet of the solution from the nozzle 14a strikes only the sucked portion of the brain tumor N. Thus the brain tumor N is crushed into pieces little by little, and the individual crushed and separated tumor pieces are sucked and removed by the suction tube 16. Since the affected tissue N is crushed and sucked only within the suction tube 16, effective crushing and removing of the tissue can be achieved with maximum safety.

Figure 3:
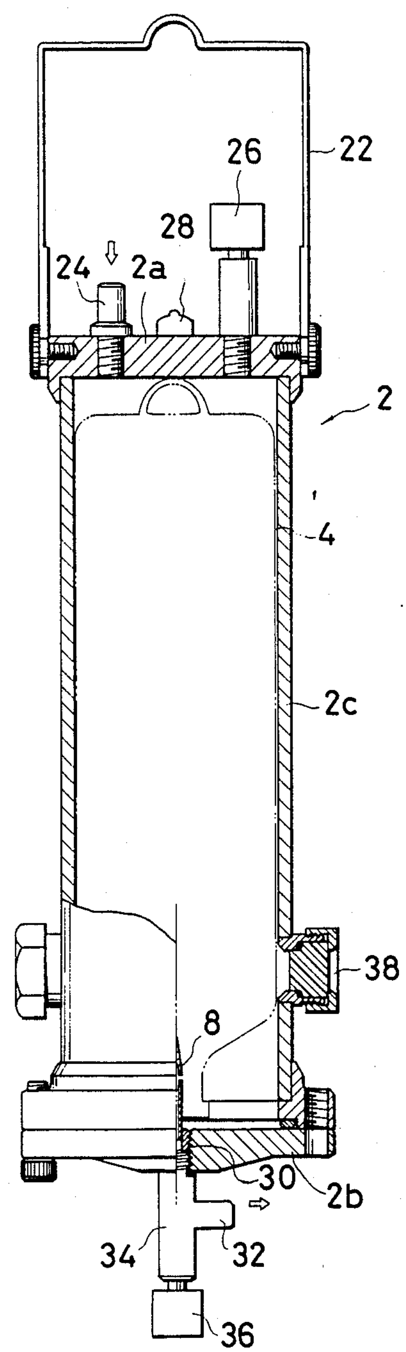
FIG. 3 is an enlarged front elevational view, partially in cross section, of a pressure chamber of FIG. 1.

As shown in FIG. 3, the pressure chamber 2 includes a top plate 2a, a bottom plate 2b, and a cylindrical body 2c. The soft bottle 4 is vertically mounted in the pressure chamber 2.

A hanger 22 is attached to the top plate 2a of the pressure chamber 2 so that the pressure chamber 2 can be hung on a non-illustrated support post. The top plate 2a has an inlet 24 to which the connection tube 21 leading from the gas cylinder 18 is adapted to be connected and through which the harmless gas from the gas cylinder 18 is to be introduced into the pressure chamber 2. A discharge valve 26 is mounted on the top plate 2a for discharging the gas out of the pressure chamber 2 after the operation is finished. A safety valve 28 also is mounted on the top plate 2a; when the pressure in the pressure chamber 2 becomes higher than a predetermined value such as by accident, the safety valve 28 automatically operates to allow the gas to escape to the exterior.

The bottom plate 2b of the pressure chamber 2 has in its center a through-hole 30, through which a metal fitting 34 having at its upper end a connection probe 8 and at its side a projection 32 is fitted. To the projection 32 one end of the irrigation tube 6 is to be connected. The connection probe 8 is inserted into the soft bottle 4 via the outlet 10 thereof so that the interior of the soft bottle 4 communicates with the irrigation tube 6. A knob 36 is mounted on the lower end of the metal fitting 34 for adjusting the amount of the solution to flow from the soft bottle 4 into the irrigation tube 6.

The cylindrical body 2c of the pressure chamber 2 has in its lower portion a pair of diametrically opposed watch windows 38, 38, through which the operator can observe the interior of the pressure chamber 2.

As shown in FIGS. 4 and 5, the switch 12 includes an elongated body 12a, a rear fitting 40 detachably mounted on a rear end of the body 12a, and a connection fitting 41 attached to a rear end of the rear fitting 40. To the connection fitting 41, the other end of the irrigation tube 6 is connected. The body 12a of the switch 12 has an axial through-bore 42, in which a flexible hose 44 is inserted, and a lower bore 46 extending perpendicularly to the axial through-bore 42 and communicating therewith. Fitted in the lower bore 46 is a lock nut 48 into which an adjusting screw 49 threadedly extends. By unfastening the adjusting screw 49 and then detaching the gear fitting 40, the flexible hose 44 can be removed from the axial through-bore 42 for replacement with a new one.

The switch body 12a also has an upper bore 50 disposed in confronting relation to the lower bore 46 with respect to the axial through-bore 42. The upper bore 50 extends perpendicularly to the axial through-bore 42 and communicates therewith. In the upper bore 50, a pushing rod 54 is vertically slidably received and is normally urged upwardly by a spring 52. A support frame 56 is fixed to the top surface of the switch body 12a, covering and supporting the pushing rod 54 and the spring 52. A switch lever 58 is pivotally connected at its base to the upper end of the pushing rod 54. A top wall 62 of the support frame 56 has an upwardly bent forward end 60 serving as a fulcrum; as the forward end of the switch lever 58 is pushed downwardly, the switch lever 58 is pivotally moved about the fulcrum 60 and concurrently the base of the switch lever 58 is moved upwardly to raise the pushing rod 54. With this arrangement, while no pushing force is being exerted on the switch lever 58, the flexible hose 44 is closed as compressed by the pushing rod 54, as shown in FIG. 4, thus preventing the solution from the soft bottle 4 from passing through the flexible hose 44. When the switch lever 58 is depressed such as by gripping, the pushing rod 54 is raised to open the flexible hose 44, thereby allowing the solution to pass through the hose 44. As a result, the solution is supplied to the ejection needle 14 and is then ejected from the nozzle 14a.

A forward fitting 62 is mounted on the forward end of the switch body 12a and has a cylindrical base portion 62a removably and threadedly mounted on the forward end of the switch body 12a, and a tip projection 62c extenting forwardly from the base portion 62a via a stepped portion 62b. The tip projection 62c has a hole 64 in which the ejection needle 14 is inserted and fixed to the projection 62c. For replacing the ejection needle 14 with a new one, firstly the forward fitting 62 is removed from the switch body 12a, then the old needle 14 is removed from the hole 64 of the projection 62c, and subsequently a new needle is inserted in the hole 64. Finally the forward fitting 62 is reattached to the switch body 12a.

Since a relatively high pressure is to be used in operating the present apparatus, various parts of the apparatus must be proof against pressure.

Further, it is preferable to mount a suitable filter in the passageway of the solution in the switch 12 so that the ejection needle 14 can be prevented from getting clogged with dust.

Figure 6:
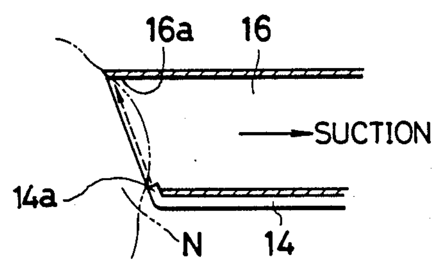
FIG. 6 is an enlarged cross-sectional view of FIG. 2, illustrating the manner in which a brain tumor is crushed and sucked by the apparatus of the invention.
Figure 7:
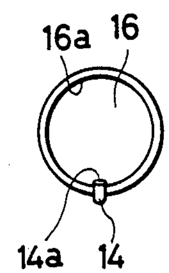
FIG. 7 is an end view of FIG. 6.

In use, the pressure in the pressure chamber 2 connected to the nitrogen cylinder 18 of a pressure of 150 $kg/cm^2$ is adjusted to 15 $kg/cm^2$. Under the pressure of 15 $kg/cm^2$ the soft bottle 4 is compressed to force the sterilized saline solution out of the bottle 4 to the switch 12 via the connection prove 8 and the irrigation tube 6. When the passageway of the solution is opened by operating the switch 12, the solution is ejected in a very small jet or stream from the nozzle 14a of the ejection needle 14 attached to the forward end of the switch 12. On the contrary, when the passageway of the solution is closed, no stream of the solution can be ejected from the nozzle 14a of the ejection needle 14. In FIG. 6, the affected tissue such as a brain tumor N is partially sucked into the tip of the suction tube 16, and only this sucked part of the brain tumor N is crushed by the pressure of the jet solution. Immediately after having been crushed, the separated tumor pieces together with the used solution are sucked by the suction tube 16 for disposal. According to the present apparatus, since the stream of solution to be ejected from the nozzle 14a is very small, it is possible to make a small incision line in the tumor, enabling a delicate operation.

Figure 8:
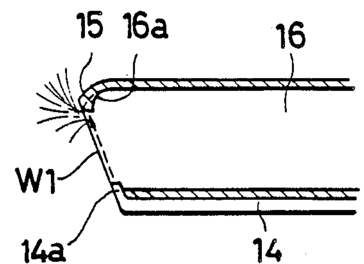
FIG. 8 is an enlarged cross-sectional view showing a modified form of the suction tube without suction.
Figure 9:
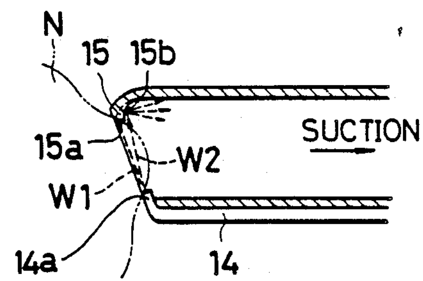
FIG. 9 is a view similar to FIG. 8, showing the modified suction tube during suction.
Figure 10:
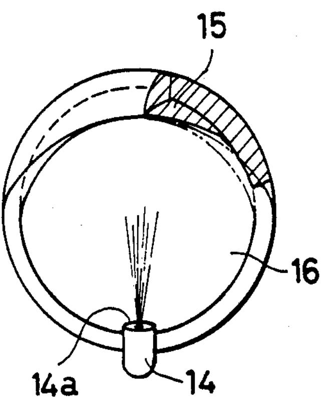
FIG. 10 is an enlarged end view, partially in cross section, of FIG. 9.

Although the surface of the confronting inside wall 16a of the suction tube 16 is cylindrical in the foregoing embodiment, it may be any alternative shape. For example, as shown in FIGS. 8 through 10, the confronting inside wall 16a may be provided with a ridge 15 having an outwardly facing taper surface 15a and an inwardly facing taper surface 15b. While the suction tube 16 is free of suction, as shown in FIG. 8, a solution stream W1 is ejected straightly from the nozzle 14a to strike the outwardly facing taper surface 15a of the ridge 15, thereby splashing outwardly of the suction tube 16. Conveniently this splashing prevents the affected part of the tissue from drying.

On the contrary, as shown in FIG. 9, while the suction tube 16 is in suction, namely, while the tumor N is being crushed and sucked, a solution stream W2 ejected from the nozzle 14a is displaced inwardly of the suction tube 16 by the force of suction to strike then the inwardly facing taper surface 15b of the ridge 15 with no outward splashing, thereby allowing normal crushing and sucking of the tumor N.

In the illustrated embodiments, the only one ejection needle 14 and hence the only one nozzle 14a are used. Alternatively two or more ejection needles and hence two or more nozzles may be used.

In case where the passageway of the solution is opened and closed by controlling the switch 12 by hand as in the illustrated example, accurate and quick opening and closing operation can be achieved. Further, operating the switch 12 by hand means that the operator's works to be done by foot can be minimized—especially in cerebral surgery, the operator must often use his foot in operating other instruments such as a microscope. Furthermore, since the switch 12 can be manufactured light in weight, it is possible to operate the apparatus easily by hand without the operator's fatigue. Because the switch 12 can be operated by either right or left hand, namely, the water-jet knife can be inserted into the trephined wound from either direction, it is possible to make an incision in the tumor even deep off the trephined wound without screening the operator's visual field.

Alternatively the switch 12 may be operated by foot. For example, the switch 12 may be replaced with only a grip, and a suitable foot-operated means for controlling passage of the solution is provided at an intermediate position of the irrigation tube 6.

With the present water-jet knife apparatus, by controlling the hole of the nozzle and also the pressure of the jet solution so as to leave the blood-vessels and concurrently by coagulating the blood-vessels by an electric knife (right-hand), it is possible to reduce loss of blood to a minimum.

In the present apparatus, since a power source is not electrical though a saline solution, which is electrically conductive, is used, there is no fear that the patient could receive so-called microshocks and macroshocks during the operation.

To sum up, the apparatus of the present invention can produce the following advantageous results: (1) an affected tissue such as a brain tumor can be crushed and removed effectively with maximum safety; (2) no injury due to local heat and hence free of a nasty smell and smoke; (3) no fear of microshocks and macroshocks; (4) reliable disinfecting or sterilizing of the solution without fear of mixing various germs with the solution; (5) no noise from the apparatus; (6) the switch (hand-piece) is small in size and light in weight and hence easy to handle; and (7) the stream of solution can be adjusted by varying the pressure to select an appropriate value within a predetermined range.

Although various minor modifications may be suggested by those versed in the art, it should be understood that we wish to embody within the scope of the patent granted hereon, all such embodiments as reasonably and properly come within the scope of our contribution to the art.

What is claimed is:

1. An aqua-stream and aspirator for crushing and removing brain tumors in cerebral surgery, comprising:

(a) a pressure chamber;

(b) a soft bottle filled with a sterilized saline solution and mounted within the pressure chamber;

(c) an irrigation tube connected at one end to an outlet of the soft bottle;

(d) an ejection needle removably connected to the other end of the irrigation tube via a switch for controlling passage of the solution through the irrigation tube; and (e) a suction tube connected to the ejection needle and extending parallel to the ejection needle;

(f) the pressure chamber being pressurized with a harmless gas so as to compress the soft bottle to eject the solution in the soft bottle from the ejection needle;

(g) the ejection needle having a bent nozzle means for outwardly directing the solution ejected from the nozzle means toward a confronting inside wall of a tip of the suction tube and for directing the ejected solution to intersect the longitudinal axis of the suction tube to thereby suck and crush brain tumor within the suction tube and to thereby permit the making of a small incision line in the brain tumor.

2. An aqua-stream and aspirator according to claim 1, wherein the tip of the suction tube has diametrically opposed first and second portions, the second portion being disposed adjacent to the nozzle, the first portion projecting beyond the second portion for receiving the solution ejected from the nozzle.

3. An aqua-stream and aspirator according to claim 1, wherein the confronting inside wall of the suction tube has at the first portion a ridge having an outwardly facing taper surface and an inwardly facing taper surface.

4. An aqua-stream and aspirator according to claim 1, wherein the confronting inside wall of the suction tube has a cylindrical surface.

5. An aqua-stream and aspirator according to claim 1, wherein the suction nozzle of the ejection needle is bent at an angle of 15° and is located outside the suction nozzle.

6. An aqua-stream and aspirator for crushing and removing brain tumors in cerebral surgery, comprising:

(a) a pressure chamber;

(b) a soft bottle filled with a sterilized saline solution and mounted within the pressure chamber;

(c) an irrigation tube connected at one end to an outlet of the soft bottle;

(d) an ejection needle removably connected to the other end of the irrigation tube via a switch for controlling passage of the solution through the irrigation tube; and (e) a suction tube extending parallel to the ejection needle;

(f) the pressure chamber being pressurized with a harmless gas so as to compress the soft bottle to eject the solution in the soft bottle from the ejection needle;

(g) the ejection needle having a bent nozzle means for directing the solution ejected from the nozzle means toward a confronting inside wall of a tip of the suction tube, wherein the confronting inside wall of the suction tube has a ridge having an outwardly facing taper surface and an inwardly facing taper surface.

* * * * *